US00PP18593P3

(12) United States Plant Patent
Higaki

(10) Patent No.: US PP18,593 P3
(45) Date of Patent: Mar. 11, 2008

(54) ***HYDRANGEA* PLANT NAMED 'TRUE BLUE'**

(50) Latin Name: *Hydrangea macrophylla*
Varietal Denomination: True Blue

(75) Inventor: Harrison Higaki, San Mateo, CA (US)

(73) Assignee: Bay City Flower Company, Half Moon Bay, CA (US)

( * ) Notice: Subject to any disclaimer, the term of this patent is extended or adjusted under 35 U.S.C. 154(b) by 0 days.

(21) Appl. No.: 11/342,081

(22) Filed: Jan. 27, 2006

(65) Prior Publication Data

US 2007/0192915 P1 Aug. 16, 2007

(51) Int. Cl.
*A01H 5/00* (2006.01)

(52) U.S. Cl. ..... Plt./250

(58) Field of Classification Search ..... Plt./250
See application file for complete search history.

*Primary Examiner*—Kent Bell
*Assistant Examiner*—June Hwu
(74) *Attorney, Agent, or Firm*—Law Offices of James R. Cypher

(57) ABSTRACT

A new and distinct cultivar of *Hydrangea macrophylla* (Thunb.) named 'True Blue' originated as a controlled cross between the cultivars 'Blue Sky' and 'Blue Danube'. The cultivar 'True Blue' has blue—R.H.S. 100 A (blue group) sepals at maturity and is distinguished from other similar cultivars of which the inventor is aware by its sepal color, and its compact and sturdy growth habit. 'True Blue' has large showy inflorescences, having both sepalous and non-sepalous florets, although at maturity the sepalous florets hide the non-sepalous florets.

7 Drawing Sheets

Botanical classification: *Hydrangea macrophylla* (Thunb.) 'True Blue'.
Variety denomination: 'True Blue'.

BACKGROUND OF THE INVENTION

This invention relates to a new and distinct cultivar of the Saxifragaceae family. The botanical name of the plant is *Hydrangea macrophylla* (Thunb.) 'True Blue'.

The new cultivar originated as a seedling from a controlled cross between the commercial variety *Hydrangea macrophylla* (Thunb.) 'Blue Danube' and the commercial variety *Hydrangea macrophylla* (Thunb.) 'Blue Sky'.

The variety 'True Blue' has pigmented sepals, and is typically grown under soil conditions with pH conditions that produce blue pigmentation. The new variety was first noticed, because it combined the desirable growth characteristics of its parents while producing flowers with sepals that have long-lasting pigmentation. The variety 'True Blue' has strong stems like its parent 'Blue Sky' and the compactness of its parent 'Blue Danube'. The florets of 'True Blue' are also glaucescent as compared to the parent 'Blue Danube', and the panicle of 'True Blue' is significantly larger than the panicle of 'Blue Danube'.

The growth habit of 'True Blue' also distinguishes it from other varieties of *Hydrangea* that have blue sepals of which the inventor is aware. 'True Blue' is more compact and its stems sturdier than the blue, commercially available variety 'Mathilda'. The pedicels of 'True Blue' also appear to be stronger, creating a stronger panicle than 'Henriksberg', another commercially available, blue variety.

The new cultivar 'True Blue' has been successfully asexually reproduced under controlled environmental conditions at a nursery in Half Moon Bay, Calif. under the direction of the inventor over a three year period with its distinguishing characteristics remaining stable.

'True Blue' is distinguished from other blue varieties of *Hydrangea* of which the inventor is aware by the manner in which its sepals age and change color. Sepal color of 'True Blue' is predominately blue at maturity. The sepals of the very young, unopened florets are R.H.S. 145 C (yellow-green group). Then, as the florets begin to age, the sepals turn purple, and then white. The characteristic that distinguishes 'True Blue' from all other varieties known to the inventor is that as the mature sepals age and turn purple they are highly resistant to burning and turning brown, unlike many other *Hydrangeas*. This makes the flowers of the plant more attractive for longer periods of time.

Asexual reproduction was first accomplished when vegetative cuttings were taken from the initially selected plant. Examination of asexually reproduced, successive generations grown in at Half Moon Bay, Calif. show that the combination of characteristics as herein disclosed for 'True Blue' remains firmly fixed through three generations.

DESCRIPTION OF THE DRAWINGS

The accompanying drawings consist of color photographs that show the typical plant form, including the inflorescence, foliage, and sepals.

DESCRIPTION OF THE NEW PLANT

Figure 1:
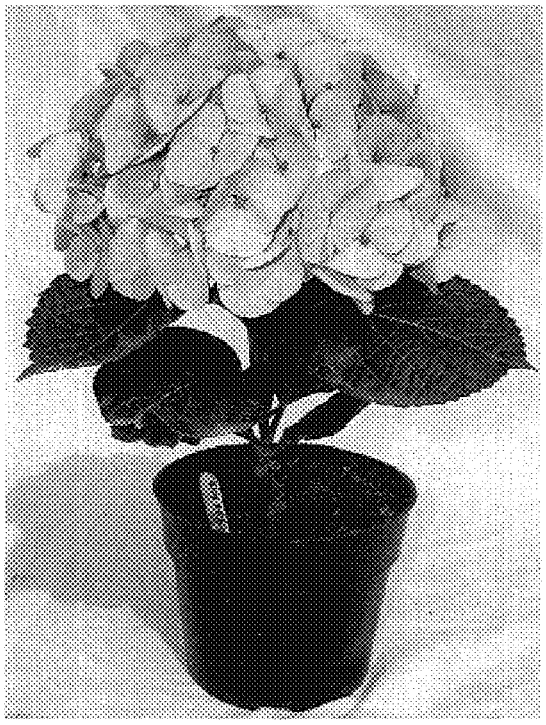
FIG. 1 is a view of the entire plant showing its form, compact growth habit, dark green foliage, inflorescence, and blue sepals. The particular plant shown has only one panicle.
Figure 2:
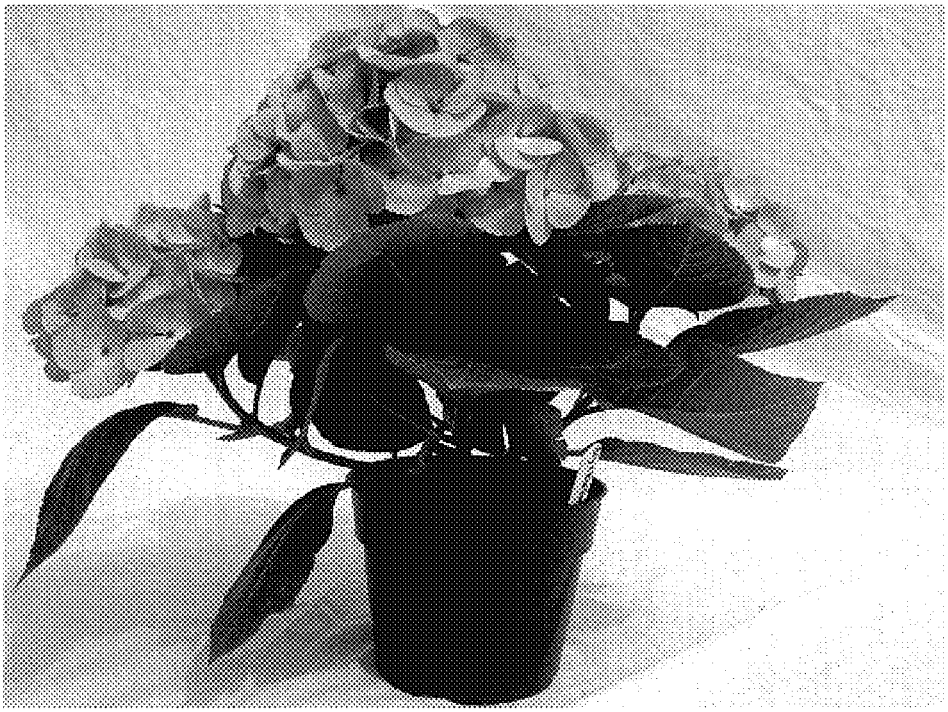
FIG. 2 is a view of the entire plant showing its form, compact growth habit, dark green foliage, inflorescence, and blue sepals. The particular plant shown has multiple panicles.
Figure 3:
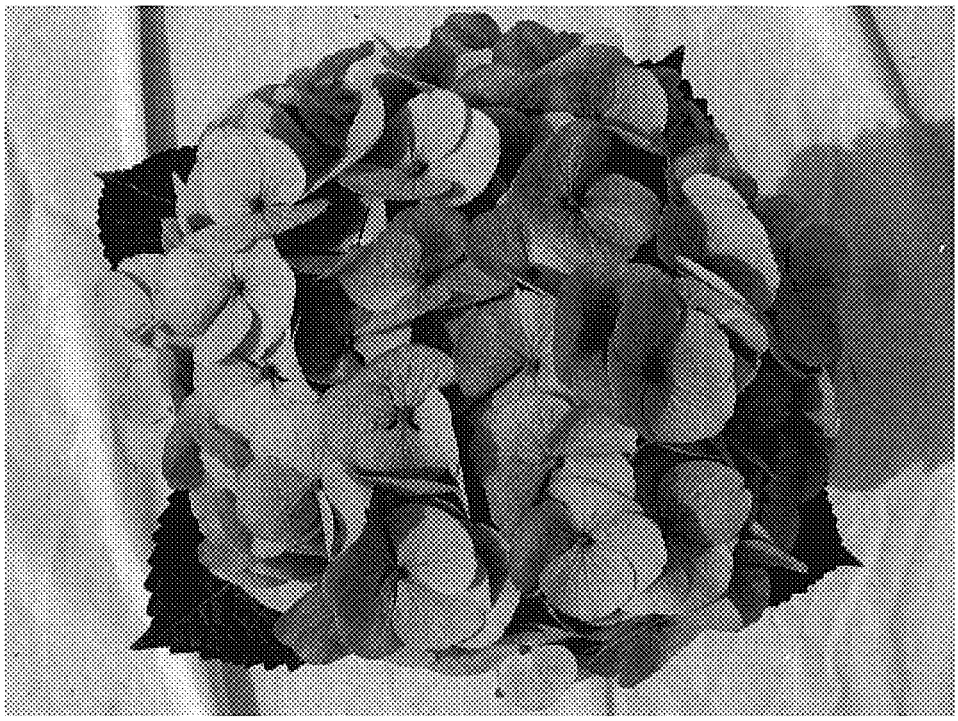
FIG. 3 is a top view of the entire plant. The particular plant shown has only one panicle.
Figure 4:
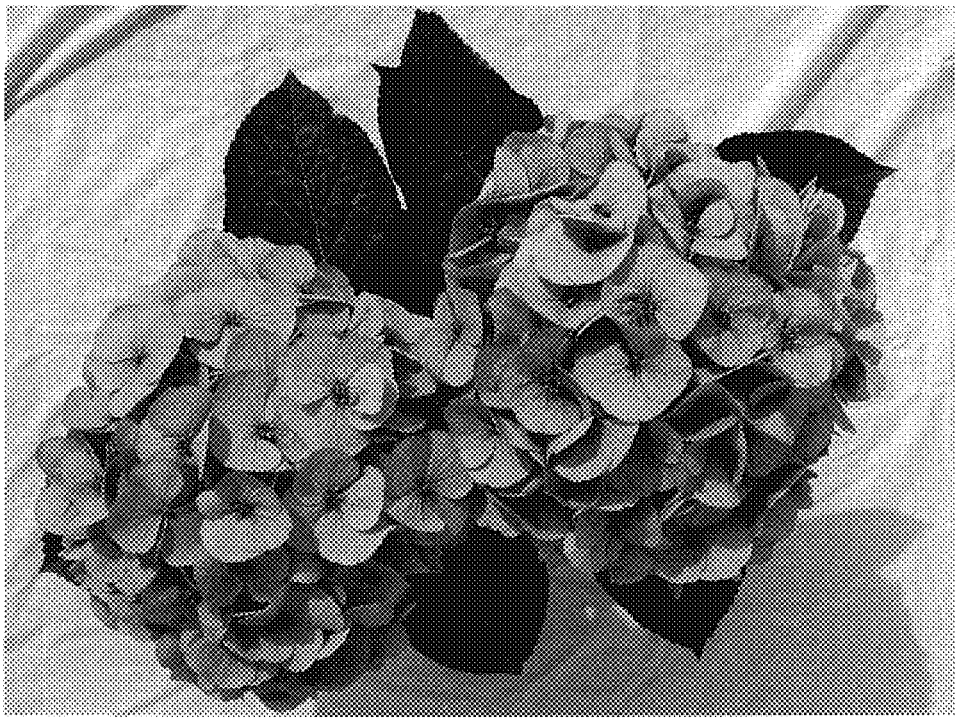
FIG. 4 is a top view of the entire plant. The particular plant shown has two panicles.
Figure 5:
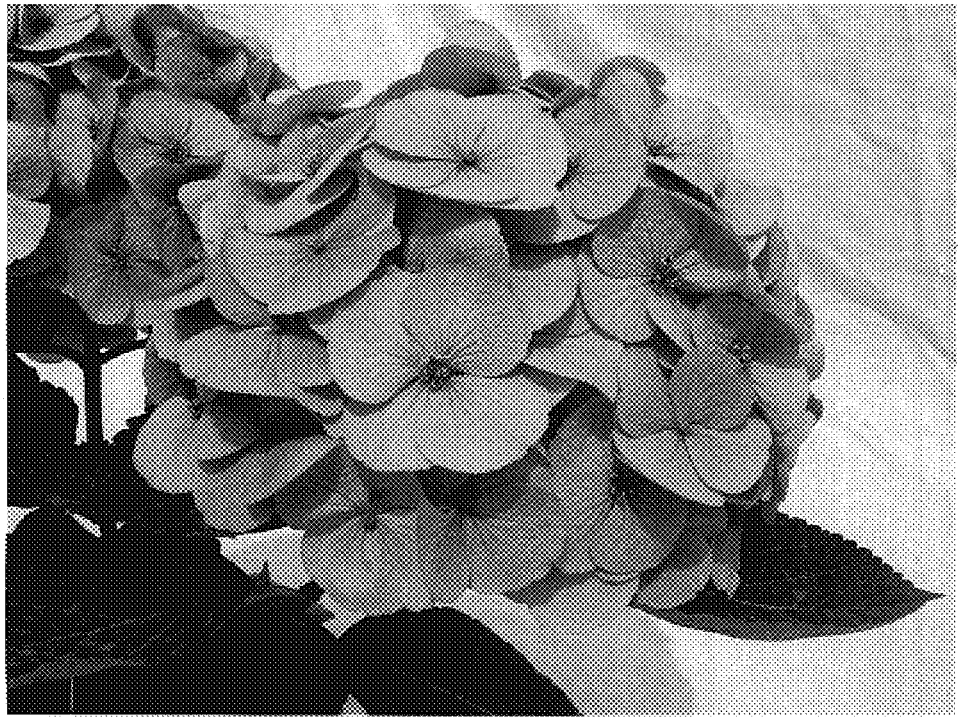
FIG. 5 is a close-up view of a panicle of the new variety, showing opened, sepalous florets.
Figure 6:
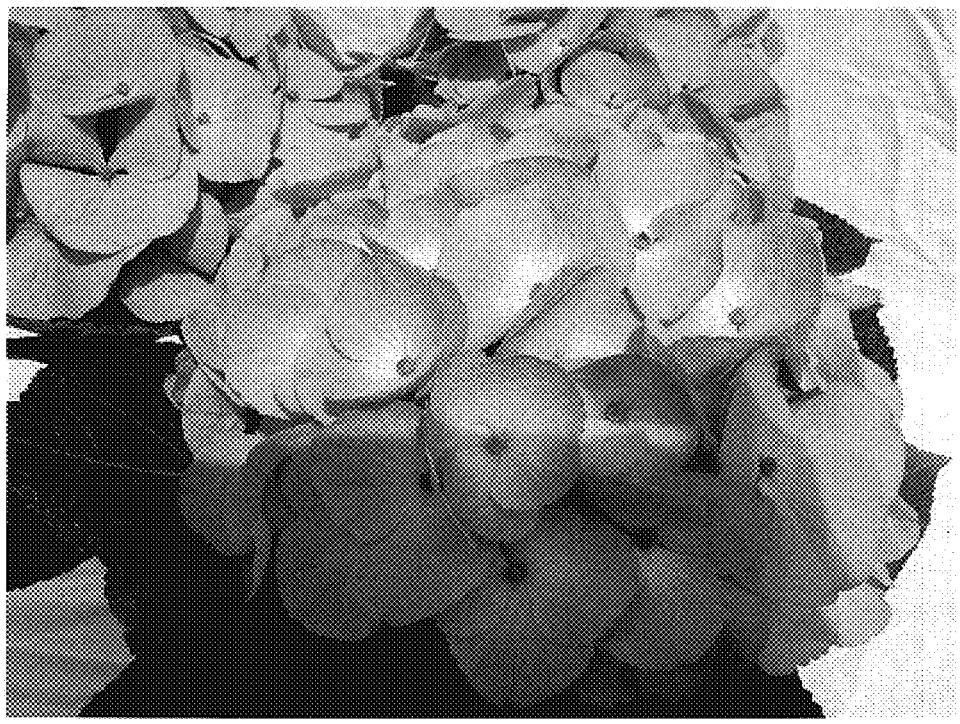
FIG. 6 is a close-up view of a panicle of the new variety. The panicle shown is still rather young. The sepalous florets have not opened yet, and the pigmentation of the sepals is not complete.
Figure 7:
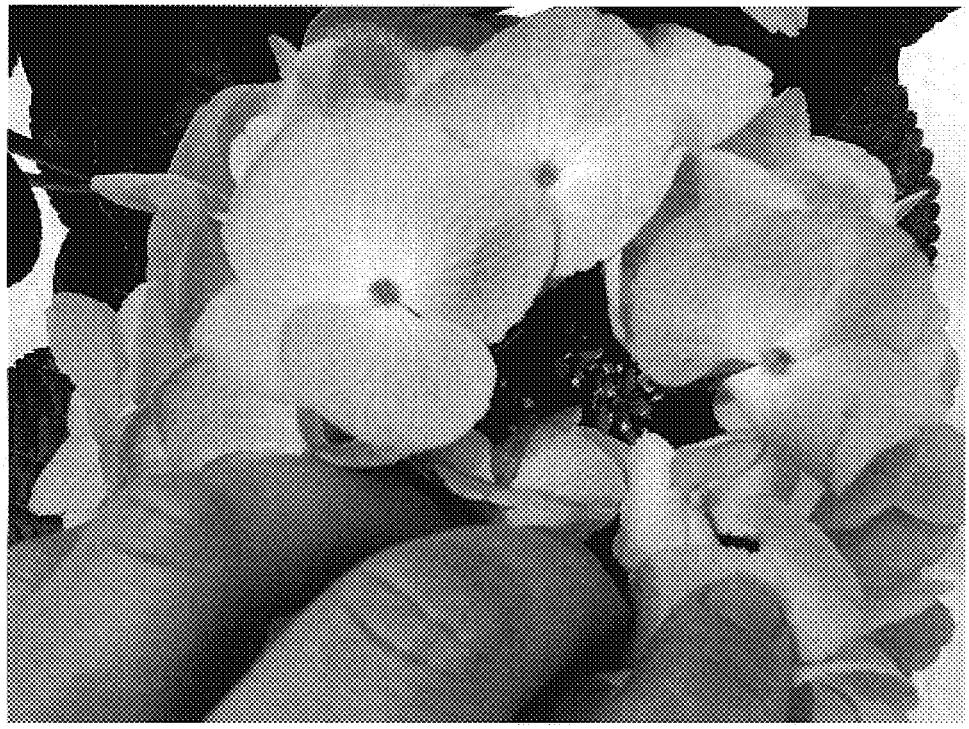
FIG. 7 is a close-up view of a panicle of the new variety. Sepalous florets have been moved to show the non-sepalous florets which are normally hidden by the sepalous florets.
Figure 8:
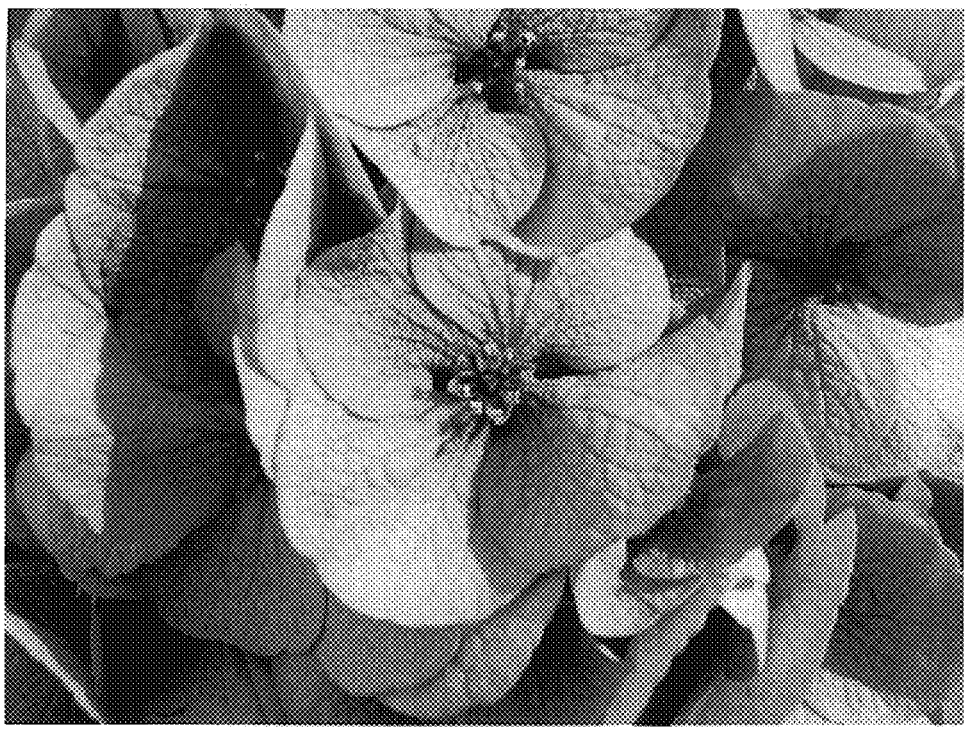
FIG. 8 is a close-up view of a mature floret of the new variety.
Figure 9:
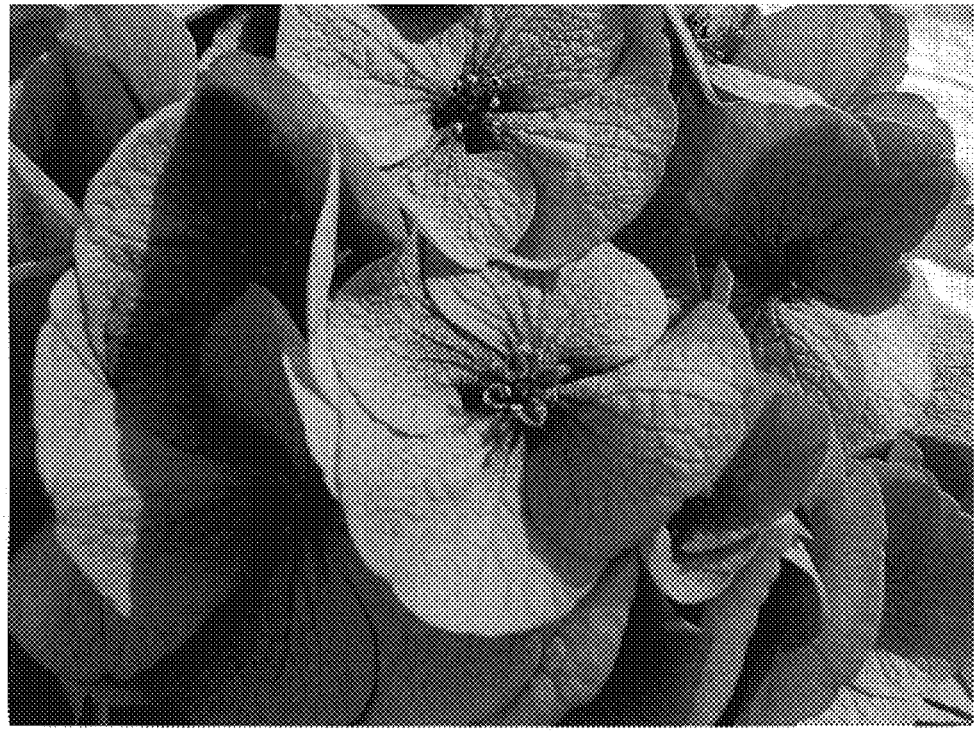
FIG. 9 is a close-up view of a mature floret of the new variety.
Figure 10:
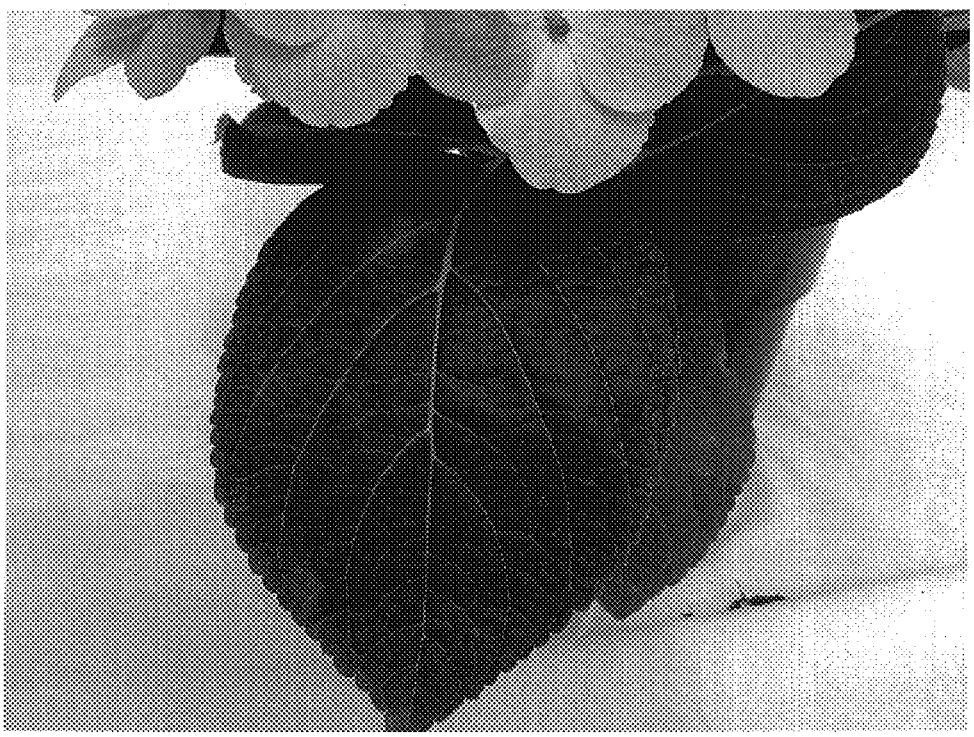
FIG. 10 is a close-up view of the adaxial surface of a mature leaf.
Figure 11:
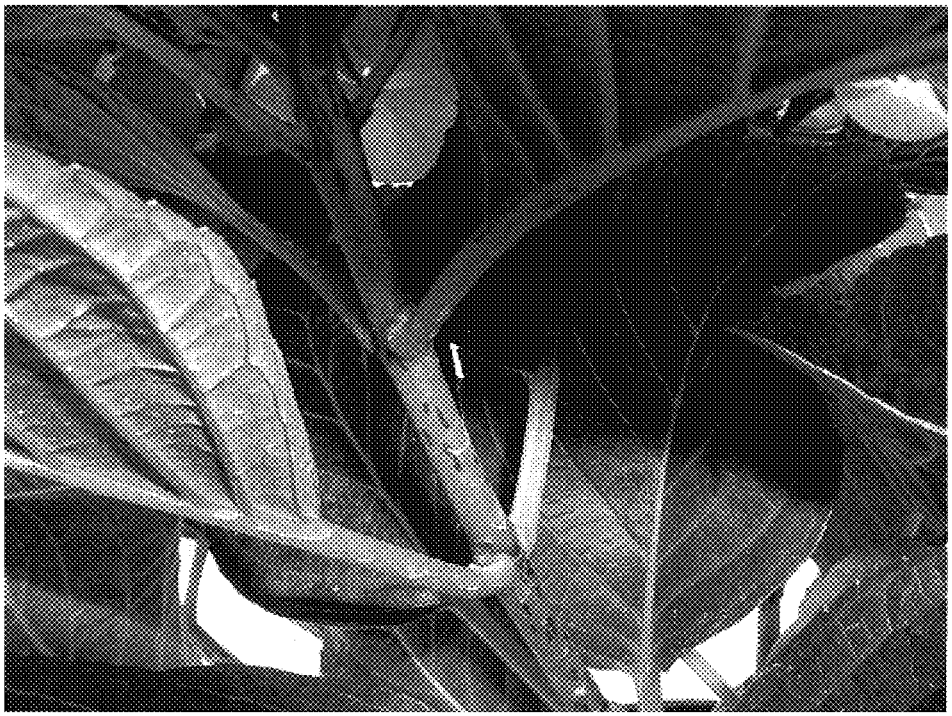
FIG. 11 is a close-up view of a non-woody portion of the stem, showing lenticels on the stem.
Figure 12:
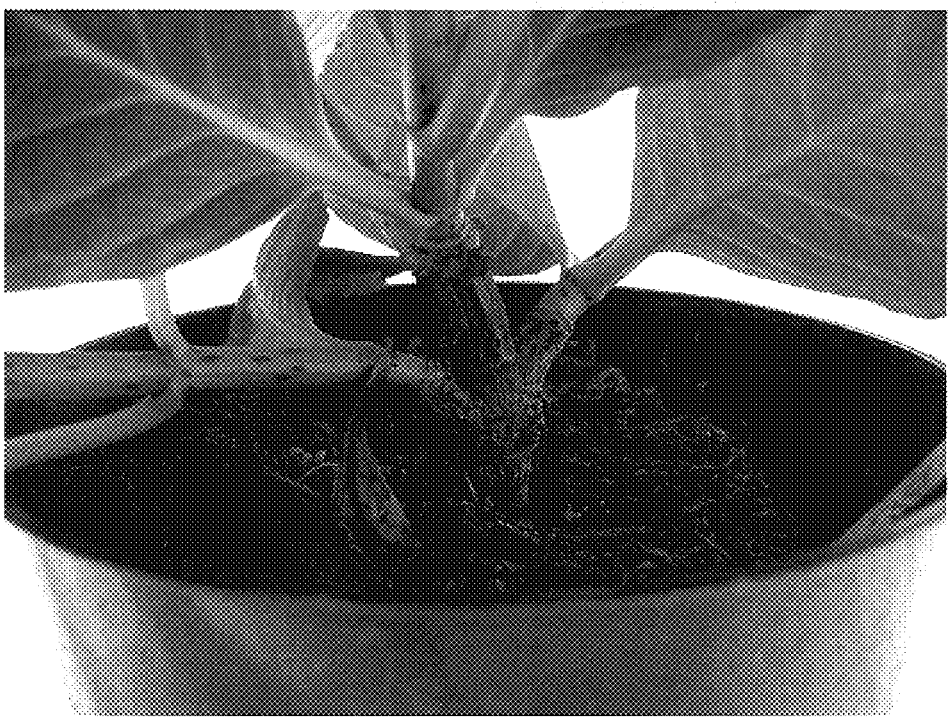
FIG. 12 is a close-up view of the base of the stem.
Figure 13:
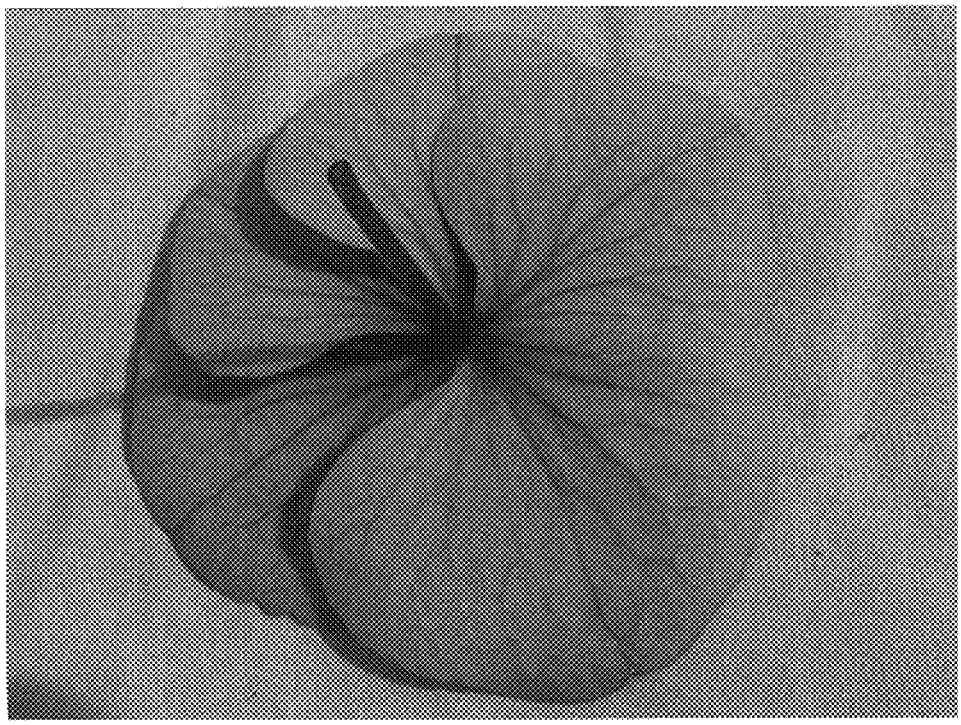
FIG. 13 is a close-up view of the underside of an individual sepalous floret.
Figure 14:
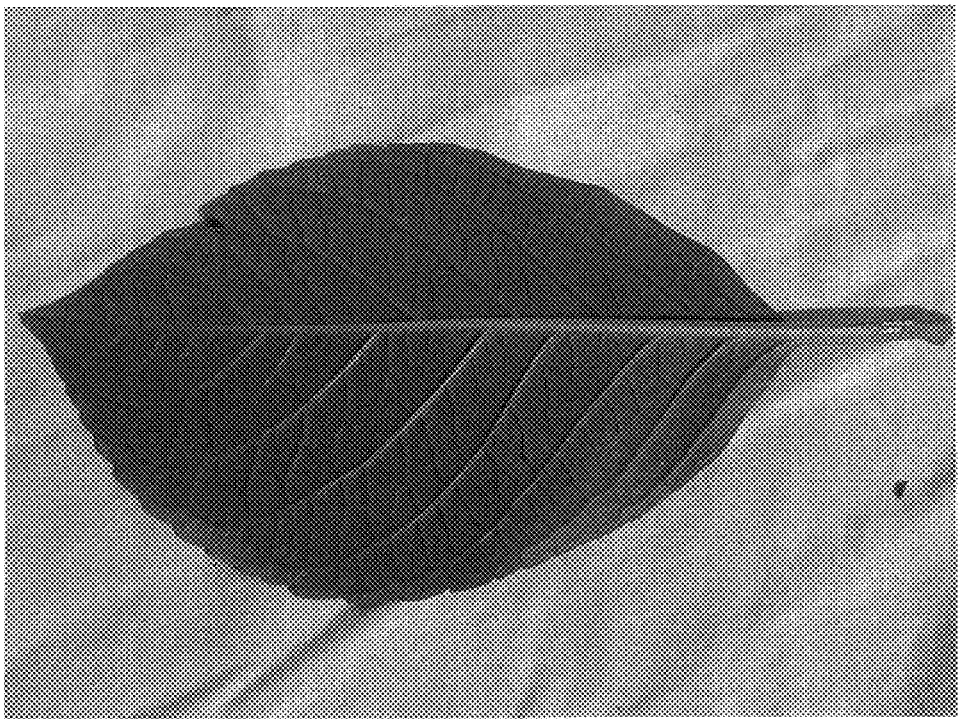
FIG. 14 is a close-up view of the abaxial surface of a mature leaf.

The plants shown in the figures are approximately 1 years old. The plant started out as cuttings, taken from the stem of a grown plant. The cuttings were placed in a 4" pot with *hydrangea* soil that would produce blue pigmentation in *Hydrangeas* that have pigmentation in their sepals.

'True Blue' has not been observed under all possible environmental conditions. The phenotype may vary significantly with variations in environment such as temperature, light intensity and day length. Color determinations were made with The Royal Horticultural Society (R.H.S.) Colour Chart.

THE PLANT

Origin: Controlled cross.

*Parents.* —*Hydrangea macrophylla* (Thunb.) 'Blue Danube' (unpatented) and *Hydrangea macrophylla* (Thunb.) 'Blue Sky' (unpatented).

*Botanic classification.* —*Hydrangea macrophylla* (Thunb.) 'True Blue'.

Form: Upright, compact shrub. A typical plant with a mature inflorescence that is ready for sale is approximately 17" high and has a diameter of 16" when grown in a 4" pot with appropriate soil amendments.

Growth: Upright, vigorous growth habit. Inflorescence is large. The plant branches easily with shoots forming at the base of the plant. Lateral branches are similar in appearance and form to the main stems.

Stems: Lenticels are present. Lenticels are very narrow, less than 0.5 mm wide, and range in length from 1 mm to 6 mm long. Lenticels are R.H.S. 59A (red-purple group). Stems become woody as they age. Young stems, less than a year, old are glabrous. The color of typical young stems and young lateral branches is R.H.S. 145 A (green group). Woody stems are R.H.S. 199 D (grey-brown group) and glabrous.

Foliage: Abundant. Leaves are opposite on stem and lateral branches.

*Shape of leaf.*—Elliptic with acute base and apex. Margins are serrate.

*Texture.*—*Glabrous; veins dominate on the underside of the leaf and are sunken on the leaf surface.*

*Color.*—Mature leaves have an upper side that is R.H.S. 147 A (yellow-green group), and an under side that is R.H.S. 147 B (yellow-green group). The upper side of younger leaves can be a little lighter at R.H.S. 137 A (green group). The veins of mature leaves are R.H.S. 145 C (yellow-green group) whether viewed from the top or the bottom of the leaf. Leaves are pinnately veined. The midvein and veins branching off the midvein are large and prominent on the underside of the leaves. Leaf petioles are glabrous and R.H.S. 145 A (green group). The blades of small mature leaves are approximately 4.5" long and 3.25" wide, while large mature leaves have blades that are as long as 7.5" long and as wide as 6.5". Petioles can be as long as 1.5" to 2".

BUDS

Form: Globose with 4 to 5 connate petals. Buds in the very center of the inflorescence are non-sepalous. The majority of buds have sepals. They are approximately 1 mm by 1 mm. Very young floret buds are R.H.S. 145C (yellow-green group).

Aspect: Smooth.

Arrangement: Borne on branched panicles.

INFLORESCENCE

Form: Paniculate. Terminal. As many as 100 or more individual flowers (florets) per inflorescence. Both sepalous florets and non-sepalous florets borne on same panicle with the sepalous florets hiding the non-sepalous florets, when the inflorescence reaches maturity. An inflorescence with 100 florets may have as many as 85 sepalous florets and 15 non-sepalous florets. Flowers do not produce a fragrance. The peduncle or panicle for the inflorescence is strong and upright. The uppermost portions of the pedicels for the individual florets are predominately blue — R.H.S. 94 A (violet-blue group) at maturity. The peduncle for the inflorescence is the same color as the stem R.H.S. 145 A (green group) and the lower portions of the pedicels for the individual florets are R.H.S. 145 A (green group). The peduncle and pedicels are glabrous. Peduncle and pedicel length varies due to the morphology of the paniculate inflorescence.

Size of Inflorescence: Large. Individual inflorescence size is dependent on the number of florets. A typical inflorescence can grow as large as 9" in diameter, and 4" high.

Shape: Clusters of numerous small florets; sepalous florets are flat and overlapping one another. Sepals are persistent.

Appearance: Showy.

FLORETS

*General.*—The non-sepalous florets at the center of the inflorescence open first. Non-sepalous florets are typically 7 mm in diameter with petals that are 3 mm long, 1.5 mm wide, and R.H.S. 100 A (blue group). Sepalous florets are perfect and complete, although petals, stamens and ovary generally fall off as floret approaches maturity. Sepalous florets are typically 6.5 cm in diameter. Corolla: Generally there are 4 petals that are blue — R.H.S. 100 A (blue group). In the sepalous florets, the petals generally fall off before the inflorescence reaches maturity.

Reproductive Organs:

*Stamens.*—10 stamens. Pollen is yellow — R.H.S. 8A (yellow group). Plant produces abundant pollen. Filament is blue — R.H.S. 100 A and approximately 2 mm long. Anther is 1 mm long and is regular and basally attached.

*Stigma.*—Two to three-pronged stigma on one pistil per floret. Stigma is violet-blue — R.H.S. 93 A (violet-blue group) and barely protrudes from the ovary.

*Ovary.*—Ovary is blue — R.H.S. 100 A (blue group) and is partially inferior.

Sepalous florets:

*General.*—Veins dominate on the underside of the sepals.

*Number of sepals.*—4 or 5 sepals per floret, usually 4.

*Aspect of sepals.*—Smooth and glaucescent.

*Shape of sepals.*—Reniform with acuminate apex. Edges often wavy when the floret is young.

*Size of sepals.*—As the florets mature, the sepals enlarge and overlap each other more and more, until, often, there is no space between the sepals when the petals of the florets open. Usually 1 dominant sepal, 2 smaller but equally-sized sepals, and 1 small sepal. Largest sepal at maturity is typically 3 cm long and 2.7 cm wide, the medium sized sepals are typically 2.4 cm long by 2.3 cm wide, and the smallest sepals are typically 2.0 cm long and 2 cm wide).

*Coloration of sepals.*—Development of the blue color of the sepals at maturity starts in the tips of the petals. As the pigment at the tips of the sepals turns blue — R.H.S. 100D (blue group), the base of the sepals will be white — R.H.S. 155 A (white group). The color of the underside of the sepals may be slightly lighter. At maturity the sepals are predominantly blue — R.H.S. 100D (blue group). As the sepals age, the veins at the base of the sepals and the tips of the sepals turn violet — R.H.S. 87 C (violet group).

Fruit: None.

I claim:

1. A new and distinct *Hydrangea macrophylla* plant named 'True Blue' substantially as herein shown and described.

* * * * *